United States Patent
Rotter et al.

(10) Patent No.: US 8,111,399 B2
(45) Date of Patent: Feb. 7, 2012

(54) SYSTEM AND METHOD FOR PERFORMING PHOTOTHERMAL MEASUREMENTS AND RELAXATION COMPENSATION

(75) Inventors: Lawrence D. Rotter, Pleasanton, CA (US); David Y. Wang, Santa Clara, CA (US); Derrick Shaughnessy, San Jose, CA (US); Mark Senko, Santa Cruz, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 455 days.

(21) Appl. No.: 12/494,734

(22) Filed: Jun. 30, 2009

(65) Prior Publication Data

US 2010/0328670 A1 Dec. 30, 2010

(51) Int. Cl.
  *G01N 21/55* (2006.01)
(52) U.S. Cl. .................................................. 356/445
(58) Field of Classification Search .................. 356/445
  See application file for complete search history.

(56) References Cited

U.S. PATENT DOCUMENTS

| | | | |
|---|---|---|---|
| 6,268,916 B1 | 7/2001 | Lee et al. | |
| 6,317,216 B1 | 11/2001 | Maris | |
| 6,795,198 B1 | 9/2004 | Fuchs et al. | |
| 7,212,288 B2 * | 5/2007 | Opsal et al. | 356/432 |
| 7,280,215 B2 * | 10/2007 | Salnik et al. | 356/432 |
| 7,362,441 B2 * | 4/2008 | Opsal et al. | 356/445 |
| 7,465,591 B2 * | 12/2008 | Borden et al. | 438/16 |
| 7,646,486 B2 * | 1/2010 | Opsal et al. | 356/445 |
| 2008/0074668 A1 * | 3/2008 | Salnik et al. | 356/432 |
| 2008/0151247 A1 * | 6/2008 | Salnik et al. | 356/432 |
| 2008/0158565 A1 * | 7/2008 | Opsal et al. | 356/445 |

FOREIGN PATENT DOCUMENTS

EP 0239408 A2 9/1987

OTHER PUBLICATIONS

WO International Search Report; PCT Application No. PCT/US10/40063—International Filing Date Jun. 25, 2010; dated Feb. 8, 2011; 3 pages.

* cited by examiner

*Primary Examiner* — Roy M Punnoose
(74) *Attorney, Agent, or Firm* — Suiter Swantz pc llo

(57) ABSTRACT

A device and methods for performing a photothermal measurement and relaxation compensation of a sample are disclosed. The device may include a probe beam source, a pump beam source, a sample, and a detector array. A method may include adjusting an intensity modulated pump beam power, adjusting a probe beam power to increase a response measurement location temperature and increase a modulated optical reflectance signal, directing the intensity modulated pump beam and the probe beam along a measurement path to a response measurement location on a sample for periodically exciting a region on the sample, detecting a reflected portion of the probe beam, and calculating an implantation dose.

20 Claims, 4 Drawing Sheets

SYSTEM AND METHOD FOR PERFORMING PHOTOTHERMAL MEASUREMENTS AND RELAXATION COMPENSATION

TECHNICAL FIELD

The present invention generally relates to a device and methods for inspecting a sample, and more particularly to a device and methods for performing a photothermal measurement utilizing a Modulated Optical Reflectance-type system.

BACKGROUND

As geometries continue to shrink, manufacturers may turn to optical techniques for performing non-destructive inspection and analysis of semiconductor wafers. Wafer test metrology equipment and techniques may often be used to verify that the wafer has not been damaged by previous processing steps. By utilizing optical measurement techniques, a sample may be examined by analyzing reflected energy resulting when an optical beam is directed at a sample wafer.

One technique of optical measurement may include Modulated Optical Reflectance (MOR). A MOR-type system may be used to inspect and analyze different sample attributes, such as material composition and layer thickness. Additionally, a MOR-type system may be used to measure and analyze a dopant added to semiconductor wafers before and after activation. A MOR-type system may often be used to inspect a semiconductor wafer subsequent to an ion implantation process.

SUMMARY

A device and methods for performing a photothermal measurement and relaxation compensation of a sample are disclosed. The device may include a probe beam source, a pump beam source, a sample, a third light source, and/or a detector array.

A method may include adjusting an intensity modulated pump beam power, adjusting a probe beam power to increase a response measurement location temperature and increase a modulated optical reflectance signal, directing the intensity modulated pump beam and the probe beam along a measurement path to a response measurement location on a sample for periodically exciting a region on the sample, detecting a reflected portion of the probe beam, and calculating an implantation dose.

A method may include performing a first modulated optical reflectance measurement, blocking a short wavelength beam to avoid further modulated optical reflectance changes unrelated to relaxation, annealing a specimen with at least one of a probe beam or a third light source, performing a second modulated optical reflectance measurement, and determining a decay factor from the first modulated optical reflectance measurement and the second modulated optical reflectance measurement.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Figure 1:
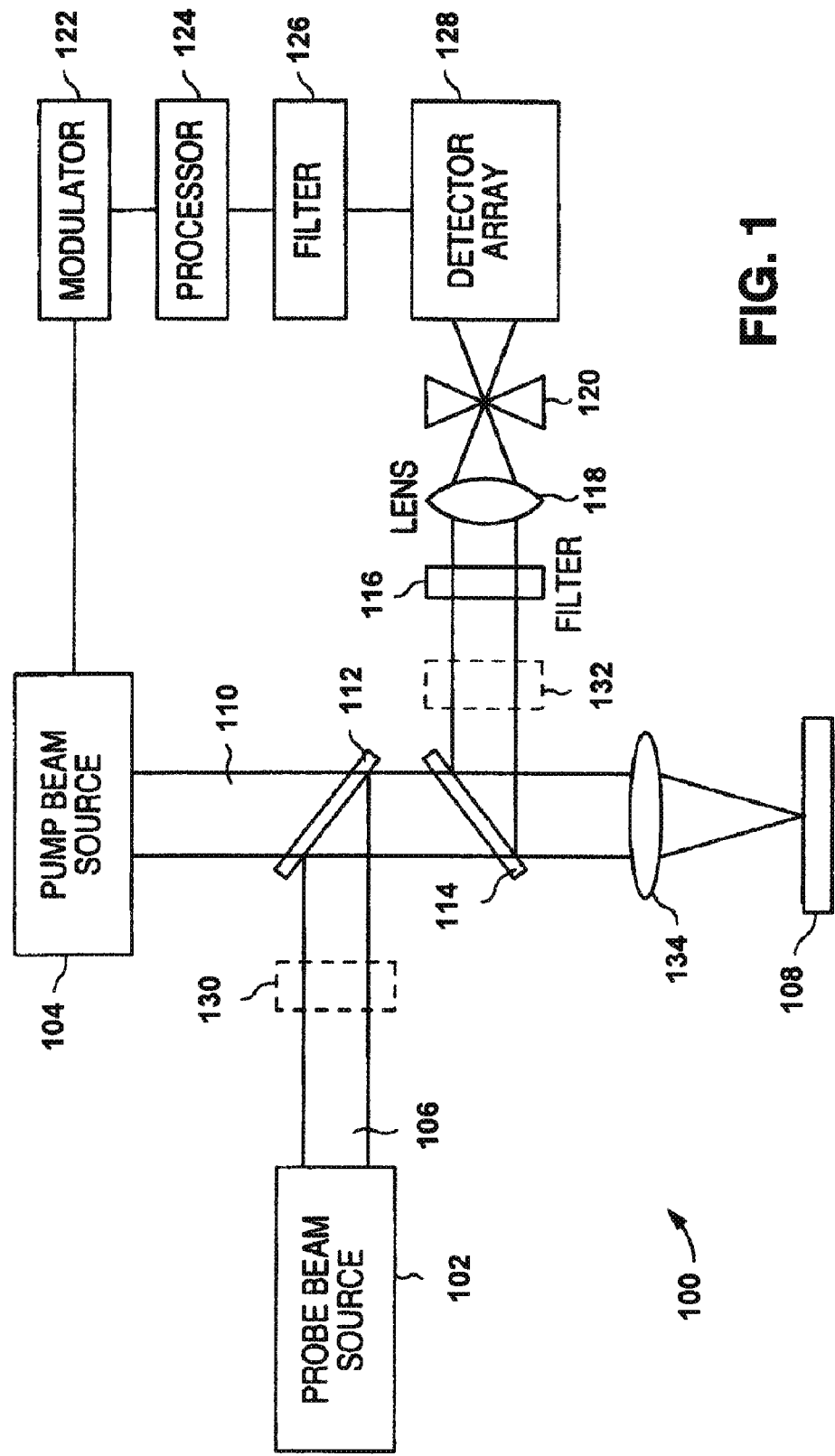
FIG. 1 illustrates an exemplary device for performing a photothermal measurement in which one or more technologies may be implemented.
Figure 2:
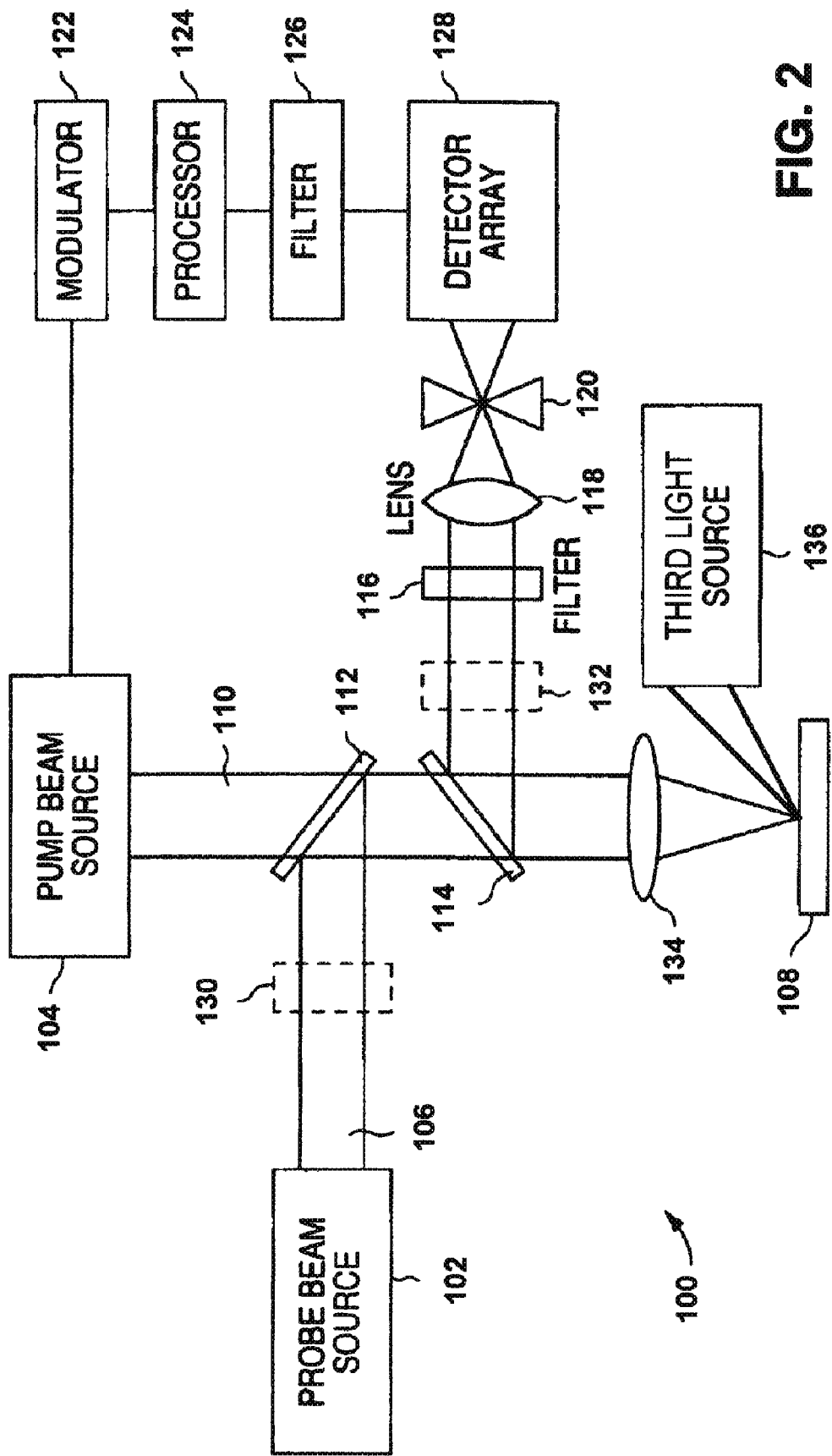
FIG. 2 illustrates an exemplary device for performing a photothermal measurement in which one or more technologies may be implemented.
Figure 3:
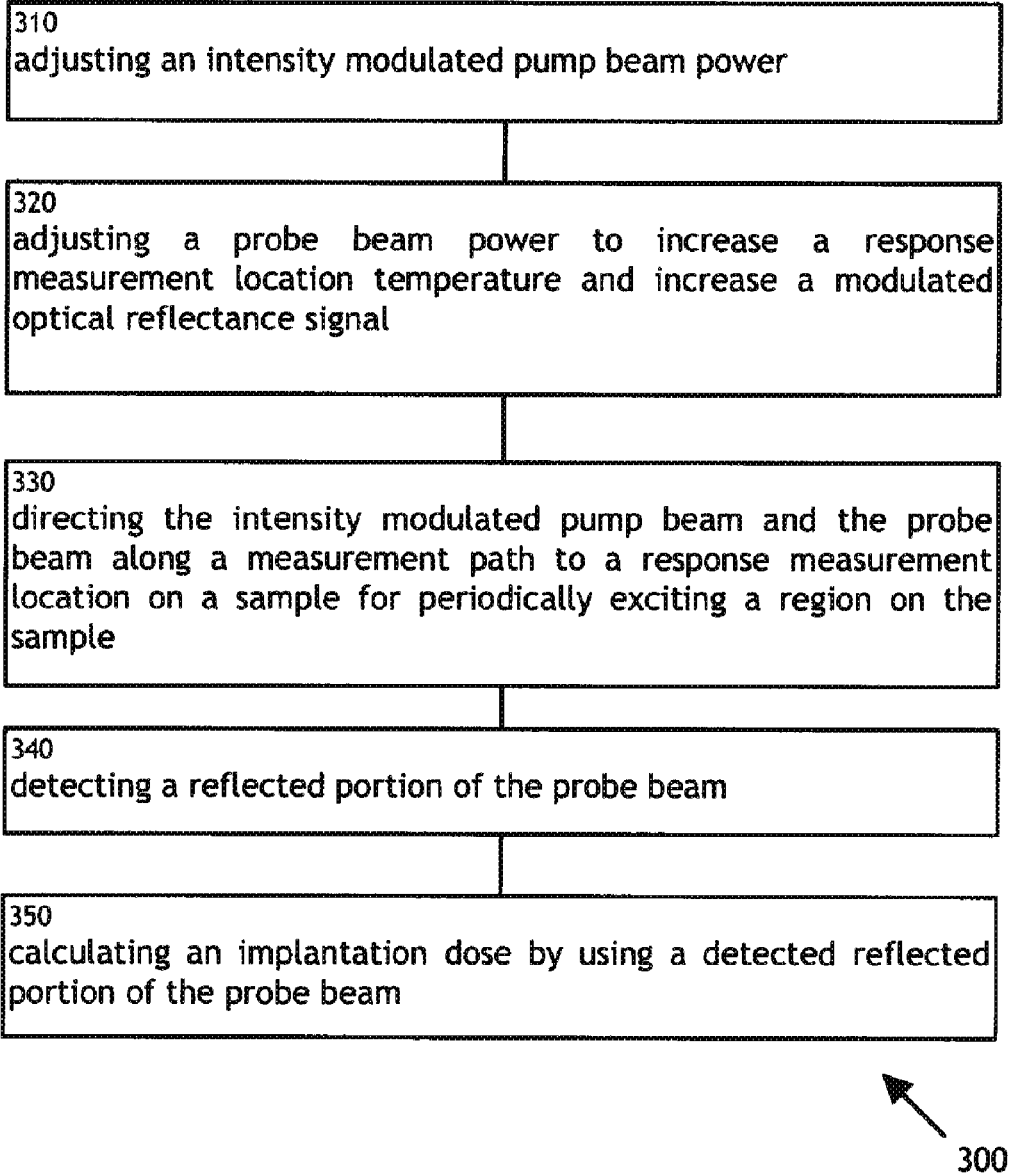
FIG. 3 illustrates a flow diagram for a method for performing a photothermal measurement.
Figure 4:
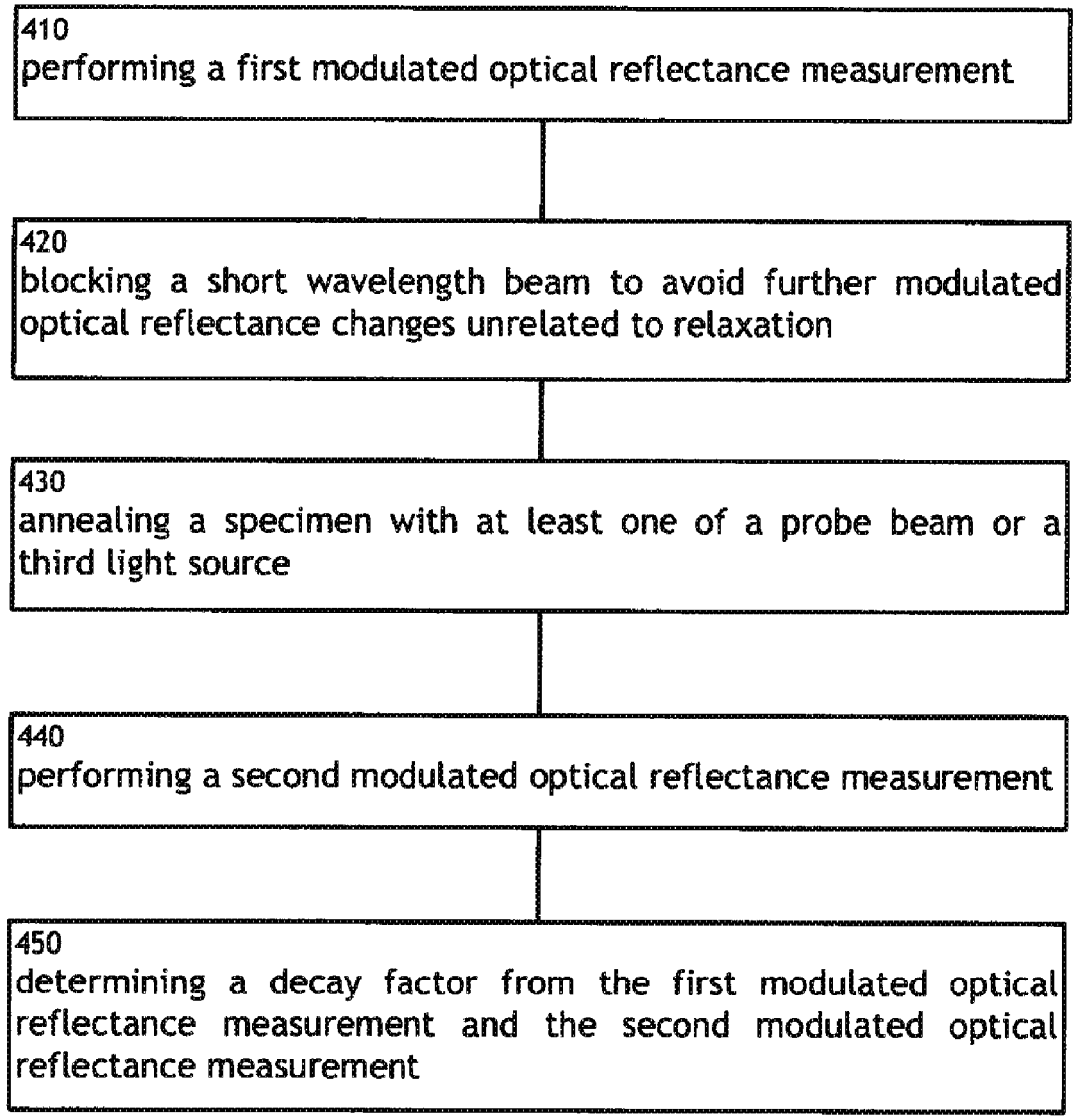
FIG. 4 illustrates a flow diagram for a method for performing a photothermal measurement.

Reference will now be made in detail to the subject matter disclosed, which is illustrated in the accompanying drawings.

Referring generally to FIGS. 1 through 4, a device 100, method 300, and method 400 for performing a photothermal measurement and relaxation compensation of a sample is disclosed. The device 100 may include a probe beam source 102, a pump beam source 104, a sample 108, and a detector array 128. Method 300 may include adjusting an intensity modulated pump beam power, adjusting a probe beam power to increase a response measurement location temperature and increase a modulated optical reflectance signal, directing the intensity modulated pump beam and the probe beam along a measurement path to a response measurement location on a sample for periodically exciting a region on the sample, detecting a reflected portion of the probe beam, and calculating an implantation dose. Method 400 may include performing a first modulated optical reflectance measurement, blocking a short wavelength beam to avoid further modulated optical reflectance changes unrelated to relaxation, annealing a specimen with at least one of a probe beam or a third light source, performing a second modulated optical reflectance measurement, and determining a decay factor from the first modulated optical reflectance measurement and the second modulated optical reflectance measurement.

A Modulated Optical Reflectance (MOR) type system may be used to measure a range of attributes including material composition and layer thickness. Additionally, a MOR-type system may be used to inspect wafers at the completion of an ion implantation process. As disclosed below, a MOR-type system may perform MOR measurements and relaxing of a sample during fabrication and/or use. The ion implantation process may damage a crystal lattice as incoming ions come to rest. This damage is often proportional to the concentration and depth of ions within the crystal lattice. A MOR-type system may make damage measurement an effective surrogate for direct measurement of dopant concentration and depth. The technology discussed below may include partial annealing of the sample, which may permit correction of the measured MOR signal due to relaxation of the sample following an ion implantation process.

Dopant activation after an ion implantation step is often performed by rapidly heating and cooling the sample, also known as annealing. During the anneal process, dopant ions diffuse away from the surface and form a concentration profile within the sample.

FIG. 1 illustrates on embodiment of device 100 including a probe beam source 102, a pump beam source 104, a sample 108, and a detector array 128. A pump beam source 104 may include a light source for generating a pump beam 110 of radiation. Some examples of pump beam source 104 may include an intensity modulated laser or incoherent light source. A gas, solid state, or semiconductor laser may be utilized, including a laser system coupled with a fiber. A lens 134 may be utilized to focus the pump beam source 104 onto a sample 108. The sample 108 may include any surface upon which the pump beam 110 and/or a probe beam 106 is directed, such as a silicon wafer. The pump beam source 104 may be directed normal to the surface of the sample 108 or at other off-axis angles. The location on the sample that is exposed to a pump beam 110 and/or pump beam source 104 may be referred to as a pump beam spot. A pump beam source 104 spot size may be from about 0.5 µm to about 5 µm. In an embodiment, pump beam source 104 may include a laser focused through a lens 134 and onto a sample 108 with a 1 µm spot size. A pump beam source 104 may be switched on and off to create an intensity-modulated pump beam. When the pump beam source 104 is switched on, the pump beam may be projected against the surface of a sample causing localized heating of the sample 108. As the laser pump is modulated, the localized heating (excitation) and subsequent cooling (relaxation) may create a train of thermal and plasma waves within the sample 108. The thermal and plasma waves may reflect and scatter off various features and interact with various regions within the sample 108 such that the flow of heat and/or plasma from the pump beam spot may be altered. In some implementations, an entire wafer may be relaxed in a special chamber and/or in a special environment utilizing temperature treatment.

The presence of the thermal and plasma waves may have a direct effect on the surface reflectivity of the sample. Features and regions below the sample surface that alter the passage of the thermal and plasma waves will therefore alter the optical reflective patterns at the sample surface. By monitoring the changes in reflectivity of the sample at the surface, information about characteristics below the surface may be investigated.

A probe beam source 102 may include a light source used to generate a probe beam 106 of radiation. The probe beam source 102 may include, for example, a laser or a broadband or white light source. A probe beam 106 may be directed at a portion of the sample illuminated by the pump beam source 104 for monitoring a surface change. In one embodiment, the pump beam source 104 may be directed toward a portion of a sample through lens 134 by a beam splitter/combiner 112. The probe beam source 102 may be directed normal to the surface of the sample 108 and/or at other angles off-axis. In another embodiment, the probe beam source 102 may be adjusted to a high power for flash annealing a sample.

The probe beam 106 may be reflected from and/or by sample 108 and deflected by a beam splitter/combiner 114 to a detector array 128. A color filter 116 may be provided for blocking pump beam light from reaching the detector array 128 and may be located between sample 108, beam splitter/combiner 104, and/or detector array 128. Additionally, lens 118 may be provided and may magnify and/or relay the reflected image of the sample to detector array 128. Optionally, a spatial filter 120 may include an aperture for controlling the size of the area of the measured sample 108 relayed to detector array 128. An additional element may be included in device 100 as element 130 and/or element 132. Some examples of additional elements may include a polarizer and/or a compensator.

A detector array 128 may record the intensity of the reflected probe beam. One example of a detector array 128 may include a photodetector. An array of photodetector elements may be used to measure the rays within the reflected and diffracted probe beam. As rays from the probe beam are measured, detector array 128 may generate an output signal. The output signal from the photodetector may be filtered by filter 126 to isolate changes that are synchronous with the pump beam modulation. In some embodiments, filtering may include a hetero-dyne and/or lock-in detector. Filtered signals from filter 126 and/or detector array 128 may be sent to processor 124 for analysis. The processor 124 may include a central processing unit and may further include a network processor and/or a digital processor. Further, processor 124 may communicate with a user interface or another computing system to output results and/or other signals to a user and/or computer peripheral.

Processor 124 may operably communicate with modulator 122. Modulator 122 may modulate a laser and/or pump beam source 104 by using a drive signal. A modulation frequency may vary from a few hertz to tens of megahertz. In one example, the modulation frequency may be one megahertz.

Method 300 may include operation 310, operation 320, operation 330, operation 340, and operation 350. Operation 310 may include adjusting an intensity modulated pump beam power. Adjusting an intensity modulated pump beam power may include reducing the pump power to a level such that MOR changes due to annealing may be sufficiently distinct from MOR changes due to exposure to short wavelength radiation, which may permit determination of the correct dopant dose. In one embodiment, a user, a signal from a computer processor, and/or modulator 122 may reduce an intensity modulated pump beam power to less than or equal to about 10 mW.

Operation 320 may include adjusting a probe beam power to increase a response measurement location temperature and increase a modulated optical reflectance signal. Adjusting a probe beam power may include increasing the probe power in order to increase the temperature at the measurement site on the sample 108 for annealing the specimen and/or increasing the MOR signal to maintain a sufficient signal to noise ratio to ensure a sufficiently repeatable dopant dose measurement. In one embodiment, a user, a signal from a computer processor, and/or modulator 122 may adjust a probe beam power greater than or equal to about 15 mW.

Operation 330 may include directing the intensity modulated pump beam and the probe beam along a measurement path to a response measurement location on a sample for periodically exciting a region on the sample. The intensity modulated pump beam, which may be synonymous with pump beam source 104, and probe beam 106 may be directed to a spot on the sample 108. The intensity modulated pump beam and the probe beam 106 may be directed and focused collinearly or may be directed along different measurement paths onto the sample 108 with lens 134. In one embodiment, probe beam source 102 and pump beam source 104 may direct a probe beam and an intensity modulated pump beam toward sample 108 through a microscope objective lens. In another embodiment, the pump beam wavelength may be shorter than the probe beam wavelength. In another embodiment, the temperature of the sample at the response measurement location may be increased from exposure to the pump beam for annealing the sample. In yet another embodiment, the intensity modulated pump beam may be directed toward sample 108 along a separate path from a probe beam 106.

In one embodiment, a third light source 136 may be utilized for annealing the sample 108. In this embodiment, the wavelength of the third light source 136 may be sufficiently long to avoid inducing MOR changes unrelated to relaxation. In this same embodiment, the exposure of the specimen may be limited to exclude and/or limit short wavelength radiation by reducing the intensity of the short wavelength beam and annealing with the third light source 136 simultaneously with the measurement of the decay factor or reducing the exposure time of the specimen to the short wavelength beam and annealing with the third light source 136 non-simultaneously with the measurement of the decay factor. Some examples of a third light source may include a laser and/or a broadband or white light source. Additionally, the third light source 136 may be directed along a separate measurement path as the pump beam 110 and/or probe beam 110 or directed along the same measurement path as the pump beam 110 and/or probe beam 110. In an embodiment, a third laser may be utilized for annealing a sample where the wavelength is about 780 nm and is directed along a measurement path separate from the pump beam path and the probe beam path, where the third laser is configured to be turned on to relax the sample before a MOR measurement. An advantage of utilizing a third light source 136 is that it does not introduce photo chemical induced transients.

Operation 340 may include detecting a reflected portion of the probe beam. In one embodiment, detector array 128 may detect a reflected portion of probe beam 106. The detector array 128 may be utilized to measure rays within a reflected and/or diffracted probe beam 106. In this embodiment, the detector array 128 may send output signals to a filter and a processor in response to the detected probe beam to a processor 124.

Operation 350 may include calculating an implantation dose. In one embodiment, processor 124 may calculate an implantation dose from output signals received from detector array 128. In one embodiment, processor 124 may calculate a decay factor by measuring a thermal wave signal over a specific time period and plotting a normalized thermal wave signal. A resultant curve may be fit to an exponential decay, and the decay factor may be calculated. A decay factor may characterize the degree of damage relaxation of the sample and/or the anneal completeness and may be used to compensate for damage relaxation and/or anneal completeness.

Method 400 may include operation 410, operation 420, operation 430, operation 440, and operation 450. Operation 410 may include performing a first modulated optical reflectance measurement. In one embodiment, device 100 may perform a short MOR measurement. The time of the MOR measurement may be a balance between a longer exposure time to increase signal to noise ratio and a shorter exposure time to decrease short wavelength induced MOR changes. In one embodiment, a MOR measurement time may be on the order of one second. Operation 420 may include blocking a short wavelength beam to avoid further modulated optical reflectance changes unrelated to relaxation. Operation 430 may include annealing a specimen with at least one of a probe beam or a third light source. In an embodiment, a third light source may anneal a sample for about ten seconds. Operation 440 may include performing a second modulated optical reflectance measurement. Operation 450 may include determining a decay factor from the first modulated optical reflectance measurement and the second modulated optical reflectance measurement.

In one embodiment, device 100, method 300, and method 400 may be implemented utilizing with a pump beam 110 directed at the specimen (sample) and adjusted to about 405 nm and about 1.0 mW, and a probe beam 106 directed at the specimen (sample) and adjusted at about 660 nm and about 17 mW. In this embodiment, the decay factor may be determined by obtaining a ratio of the signal as it would be measured after decaying ($Tw_{inf}$) versus a measurement before decaying ($Tw_0$). Annealing the sample by exposure to the probe beam 106 and/or the pump beam 110 accelerates and/or closely mimics the natural decay of the wafer. With both the probe beam 106 and pump beam 110 switched on, a measurement spot may be concentrated on and data collected as the wafer anneals. A curve from the resulting data may be fitted to one of several possible functional forms such as, but not limited to, $Tw(t)=A+B*\log(t)$ and/or $Tw(t)=A+B*\exp(-Ct)\text{erfc}(\sqrt{Ct})$, which describes the annealing process. If the change in MOR due to exposure to the short wavelength pump is non-negligible, a term to describe this effect, which may also be function of t, may be added to the model. $Tw_{inf}$ may be determined by evaluating the fitted function at a predetermined time, which may or may not be a true asymptotic infinity value. $Tw_0$ may be determined either by evaluating the fitted function at a predetermined time, which may or may not be zero, or by performing a separate measurement during which the measurement spot is moving relative to the wafer, which may minimize the anneal effect and maximize spatial averaging of the signal.

One advantage of the device 100, method 300, and method 400 may include the utilization of a short wavelength pump beam while maintaining the veracity of the decay factor. A short wavelength pump may be advantageous because it may increase the signal strength relative to a longer wavelength pump and increase the sensitivity of a MOR measurement to dopant dose over broad ranges of dopant dose. The improved sensitivity may include removal of the transition region from a plasma-dominated MOR signal to a thermal-dominated MOR signal from the dose range of interest and thus provide a monotonic signal dependence to dopant dose at low doses.

One disadvantage of previous methods is that changes may be induced in the MOR signal unrelated to relaxation, which makes determination of the decay factor difficult. This may arise when the pump laser beam is of sufficiently short wavelength, e.g., 405 nm. Exposure of the measurement site to short wavelength radiation may induce MOR changes that may be irreproducible and/or difficult to distinguish from MOR changes due to annealing. A MOR-type system may utilize two laser beams incident on the specimen—a modulated pump and an un-modulated probe. In previous methods, MOR techniques have used the relatively high intensity pump beam and a lower intensity probe beam. The method disclosed herein is counter-intuitive with respect to previous methods as the pump beam intensity in previous methods has been higher than the probe beam intensity.

In the present disclosure, the methods disclosed may be implemented as sets of instructions or software readable by a device. Further, it is understood that the specific order or hierarchy of steps in the methods disclosed are examples of exemplary approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed is:

1. A method for evaluating a semiconductor sample during fabrication, comprising:
    adjusting an intensity modulated pump beam power;
    adjusting a probe beam power to increase a response measurement location temperature and increase a modulated optical reflectance signal;

directing the intensity modulated pump beam and the probe beam along a measurement path to a response measurement location on a sample for periodically exciting a region on the sample;

detecting a reflected portion of the probe beam; and calculating an implantation dose by using a detected reflected portion of the probe beam.

2. The method in claim 1, wherein the adjusting an intensity modulated pump beam power comprises:

inducing an amorphous phase to crystalline phase change.

3. The method in claim 1, wherein the adjusting an intensity modulated pump beam power comprises:

adjusting an intensity modulated pump beam power less than approximately 10 mW.

4. The method in claim 1, wherein the adjusting a probe beam power to increase a response measurement location temperature and increase a modulated optical reflectance signal comprises:

adjusting the probe beam greater than approximately 15 mW.

5. The method in claim 1, wherein the adjusting a probe beam power to increase a response measurement location temperature and increase a modulated optical reflectance signal comprises:

increasing modulated optical reflectance signal to maintain a signal to noise ratio to make a repeatable dose measurement.

6. The method in claim 1, wherein the directing the intensity modulated pump beam and the probe beam along a measurement path to a response measurement location on a sample for periodically exciting a region on the sample comprises:

directing the intensity modulated pump beam where the pump beam wavelength is shorter than the probe beam wavelength.

7. The method in claim 1, wherein the directing the intensity modulated pump beam and the probe beam along a measurement path to a response measurement location on a sample for periodically exciting a region on the sample comprises:

increasing temperature at the response measurement location for annealing a specimen.

8. The method in claim 1, wherein the directing the intensity modulated pump beam and the probe beam along a measurement path to a response measurement location on a sample for periodically exciting a region on the sample comprises:

selecting at least one of a pump beam spot size or a probe beam spot size to be from about 0.5 µm to about 5 µm.

9. The method in claim 1, wherein the directing the intensity modulated pump beam and the probe beam along a measurement path to a response measurement location on a sample for periodically exciting a region on the sample comprises:

directing the intensity modulated pump beam and the probe beam to a silicon wafer.

10. The method in claim 1, wherein the calculating an implantation dose comprises:

calculating a decay factor.

11. The method in claim 1, further comprising:

relaxing an entire semiconductor wafer prior to performing a measurement.

12. The method in claim 1, further comprising:

utilizing a third light source to anneal the sample.

13. The method in claim 12, wherein the utilizing a third light source to anneal the sample comprises:

limiting exposure of the sample to short wavelength radiation by reducing the intensity of a short wavelength beam and annealing with the third light source simultaneously with measuring a decay factor.

14. The method in claim 12, wherein the utilizing a third light source to anneal the sample comprises:

limiting exposure of the sample to short wavelength radiation by reducing exposure time of the sample to a short wavelength beam and annealing with the third light source non-simultaneously with the measurement of the decay factor.

15. The method in claim 12, wherein the utilizing a third light source to anneal the sample comprises:

utilizing a third laser at 780 nm that anneals the sample in a separate path from a pump beam path and a probe beam path.

16. The method in claim 12, wherein the utilizing a third light source to anneal the sample comprises:

utilizing a third laser configured to be turned on to relax the sample before a MOR measurement.

17. A method for evaluating a semiconductor sample during fabrication, comprising:

performing a first modulated optical reflectance measurement;

blocking a short wavelength beam to avoid further modulated optical reflectance changes unrelated to relaxation;

annealing a specimen with at least one of a probe beam or a third light source;

performing a second modulated optical reflectance measurement; and determining a decay factor from the first modulated optical reflectance measurement and the second modulated optical reflectance measurement.

18. The method in claim 17, wherein the performing a first modulated optical reflectance measurement comprises:

exposing the sample for about one second.

19. The method in claim 17, wherein the annealing a specimen with at least one of a probe beam or a third light source comprises:

annealing the sample for about ten seconds.

20. A device for evaluating a semiconductor sample, comprising:

means for adjusting an intensity modulated pump beam power;

means for adjusting a probe beam power to increase a response measurement location temperature and increase a modulated optical reflectance signal;

means for directing the intensity modulated pump beam and the probe beam along a measurement path to a response measurement location on a sample for periodically exciting a region on the sample;

means for detecting a reflected portion of the probe beam; and means for calculating an implantation dose.

* * * * *